(12) United States Patent
Hirata et al.

(10) Patent No.: US 9,970,043 B2
(45) Date of Patent: *May 15, 2018

(54) PROCESS FOR PRODUCING OPTICALLY ACTIVE 2-ALKYL-1,1,3-TRIALKOXYCARBONYLPROPANE

(71) Applicant: GENENTECH, INC., South San Francisco, CA (US)

(72) Inventors: Norihiko Hirata, Suita (JP); Kazuhiro Yamauchi, Ibaraki (JP)

(73) Assignee: GENENTECH, INC., South San Francisco, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/365,760

(22) Filed: Nov. 30, 2016

(65) Prior Publication Data

US 2017/0145468 A1   May 25, 2017

Related U.S. Application Data

(63) Continuation of application No. 14/618,900, filed on Feb. 10, 2015, now abandoned, which is a continuation of application No. 12/599,338, filed as application No. PCT/JP2008/058991 on May 9, 2008, now Pat. No. 8,969,051.

(30) Foreign Application Priority Data

May 14, 2007 (JP) .................................. 2007-127704
May 29, 2007 (JP) .................................. 2007-141542
Mar. 27, 2008 (JP) .................................. 2008-083302

(51) Int. Cl.
 *C12P 7/62* (2006.01)
 *C12P 41/00* (2006.01)
 *C12N 9/18* (2006.01)

(52) U.S. Cl.
 CPC ............... *C12P 41/005* (2013.01); *C12P 7/62* (2013.01); *C12N 9/18* (2013.01)

(58) Field of Classification Search
 CPC ............. C12P 7/62; C12P 41/005; C12N 9/18
 USPC ......................................................... 435/135
 See application file for complete search history.

(56) References Cited

U.S. PATENT DOCUMENTS

| 8,969,051 B2 | 3/2015 | Hirata et al. |
| 2008/0026433 A1 | 1/2008 | Hedvati et al. |
| 2015/0218602 A1 | 8/2015 | Hirata |

FOREIGN PATENT DOCUMENTS

| JP | H11209345 A | 8/1999 |
| JP | 2006061112 A | 3/2006 |
| WO | 2006000904 A2 | 1/2006 |
| WO | 2007143113 A2 | 12/2007 |

OTHER PUBLICATIONS

EP Supplemental Search Report, dated Nov. 5, 2010 in EP Application No. 08 75 2844.4.
Evans, et al., "Enantioselective Lewis Acid Catalyzed Michael Reactions of Alkylidene Malonates Catalsis by C2-Symmetric Bis(oxazoline) Copper (II) Complexes in the Synthesis of Chiral, Differentiated Glutarate Esters", J. Am. Chem. Soc., vol. 122 (38), 9134-9142 (2000).
Martinez, et al., "Development of a Chemoenzymatic Manufacturing Process for Pregabalin", Organic Process Research and Development vol. 12 (3), 392-398 (2008).
Witkowski, et al., "Conversion of a beta-ketoacyl synthase to a malonyl decarboxylase by replacement of the active-site cysteine with glutamine", Biochemistry, 38 (36), 11643-11650 (1999).
Written Opinion, dated Nov. 23, 2010 in EP Application No. EP 08752844.4.

*Primary Examiner* — Robert B Mondesi
*Assistant Examiner* — Mohammad Y Meah
(74) *Attorney, Agent, or Firm* — Viksnins Harris Padys Malen LLP

(57) ABSTRACT

A process for producing an optically active 2-alkyl-1,1,3-trialkoxycarbonylpropane (2), comprising a step of asymmetric hydrolysis of 2-alkyl-1,1,3-trialkoxycarbonylpropane (1) by using an enzyme capable of selectively hydrolyzing an ester moiety of either one enantiomer of 2-alkyl-1,1,3-trialkoxycarbonylpropane (1), or by using a culture of a microorganism capable of producing the enzyme or a treated object thereof.

9 Claims, No Drawings

PROCESS FOR PRODUCING OPTICALLY ACTIVE 2-ALKYL-1,1,3-TRIALKOXYCARBONYLPROPANE

CROSS-REFERENCE TO RELATED APPLICATIONS

This application is a continuation of U.S. patent application Ser. No. 14/618,900, filed Feb. 10, 2015, now abandoned, which is a continuation of U.S. patent application Ser. No. 12/599,338, filed Nov. 9, 2009, now issued as U.S. Pat. No. 8,969,051, which is a 371 of International Patent Application No. PCT/JP2008/058991, filed May 9, 2008, which was published on Nov. 20, 2008 under International Publication No. WO 2008/140127 A1. The entire content of the applications referenced above are hereby incorporated by reference herein. This application also claims priority to Japanese Patent Application No. 2007-127704, filed May 14, 2007, Japanese Patent Application No. 2007-141542, filed May 29, 2007, and Japanese Patent Application No. 2008-083302, filed Mar. 27, 2008.

TECHNICAL FIELD

The present invention relates to a process for producing an optically active 2-alkyl-1,1,3-trialkoxycarbonylpropane.

BACKGROUND ART

An optically active 2-alkyl-1,1,3-trialkoxycarbonylpropane is a compound useful as a material for formation of an asymmetric carbon atom in synthesis of natural products, pharmaceuticals and so on.

Heretofore, as a method for producing such an optically active 2-alkyl-1,1,3-trialkoxycarbonylpropane, for example, a method of addition of a silyl enolate to an alkylidenemalonate in the presence of an asymmetric copper catalyst (Non-patent document 1) is known. By ester-exchange of the thioester obtained in this production method, an optically active 2-alkyl-1,1,3-trialkoxycarbonylpropane can be obtained. In this method, however, a halogenated solvent is used, and a low temperature condition is required for improving the optical purity of the objective substance. Additionally, even when the reaction is conducted at −78° C., the optical purity is at most 93% ee (43% ee when the alkyl group that binds to the carbon atom serving as optically-active center is a methyl group), so that this method is not necessarily satisfactory from the industrial view.

[Non-patent document 1] J. Am. Chem. Soc., 122, 9134 (2000)

DISCLOSURE OF THE INVENTION

In view of the above, the present inventors have studied intensely about a process for producing an optically active 2-alkyl-1,1,3-trialkoxycarbonylpropane by hydrolyzing a racemic form of 2-alkyl-1,1,3-trialkoxycarbonylpropane as a material in an optically selective manner using various kinds of enzymes under an ordinary enzymatic reaction condition, and have found that both isomers of the optically active 2-alkyl-1,1,3-trialkoxycarbonylpropane can be produced easily with excellent efficiency.

Specifically, the present invention provides the following [1]-[11].

[1] A process for producing an optically active 2-alkyl-1,1,3-trialkoxycarbonylpropane represented by Formula (2):

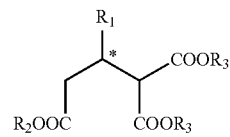

(wherein, $R_1$, $R_2$ and $R_3$, which may be the same or different, represent a C1-C4 alkyl group, and * represents that the carbon atom is an asymmetrical center) comprising a step of asymmetric hydrolysis of an 2-alkyl-1,1,3-trialokoxycarbonylpropane represented by Formula (1):

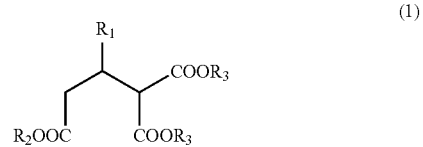

(wherein $R_1$, $R_2$ and $R_3$ are as defined above) by using an enzyme capable of selectively hydrolyzing an ester moiety of either one enantiomer of the 2-alkyl-1,1,3-trialkoxycarbonylpropane represented by Formula (1), or a culture of a microorganism capable of producing the enzyme or a treated object thereof.

[2] The process according to [1], wherein $R_2$ in the 2-alkyl-1,1,3-trialkoxycarbonylpropane represented by Formula (1) is a methyl group.

[3] The process according to [1], wherein $R_2$ in the 2-alkyl-1,1,3-trialkoxycarbonylpropane represented by Formula (1) is a methyl group.

[4] The process according to [1], wherein $R_3$ in the 2-alkyl-1,1,3-trialkoxycarbonylpropane represented by Formula (1) is a methyl group.

[5] The process according to [1], wherein both $R_1$ and $R_2$ in the 2-alkyl-1,1,3-trialkoxycarbonylpropane represented by Formula (1) are methyl groups.

[6] The process according to [1], wherein both $R_2$ and $R_3$ in the 2-alkyl-1,1,3-trialkoxycarbonylpropane represented by Formula (1) are methyl groups.

[7] The process according to [1], wherein all of $R_1$, $R_2$ and R3 in the 2-alkyl-1,1,3-trialkoxycarbonylpropane represented by Formula (1) are methyl groups.

[8] The process according to any one of [1] to [7], wherein the enzyme is a hydrolase originated from a microorganism of Candida or Bacillus.

[9] The process according to any one of [1] to [7], wherein the enzyme is a hydrolase originated from a microorganism of Arthrobacter globiformis, Candida cylindracea, Candida rugosa, Candida antactica, Bacillus licheniformis, Bacillus subtilis or Chromobacterium chocolatum or a thermophilic microorganism.

[10] The process according to any one of [1] to [7], wherein the enzyme is an esterase or a lipase originated from Arthrobacter strain SC-6-98-28 (FERM BP-3658) or Chromobacterium strain SC-YM-1 (FERM BP-6703).

[11] The process according to any one of [1] to [7], wherein the enzyme is a protein containing an amino acid sequence selected from the following a) to e):

a) an amino acid sequence represented by SEQ ID NO: 1 or 3;

b) an amino acid sequence i) which is encoded by a nucleotide sequence of DNA having at least 90% homology to DNA having a nucleotide sequence represented by SEQ ID NO: 2 or 4, and ii) which is an amino acid sequence of a protein capable of selectively hydrolyzing an ester moiety of either one enantiomer of the 2-alkyl-1,1,3-trialkoxycarbonylpropane;

c) an amino acid sequence i) which is encoded by a nucleotide sequence of DNA that hybridizes with DNA having a nucleotide sequence represented by SEQ ID NO: 2 or 4 under a stringent condition, and ii) which is an amino acid sequence of a protein capable of selectively hydrolyzing an ester moiety of either one enantiomer of the 2-alkyl-1,1,3-trialkoxycarbonylpropane;

d) an amino acid sequence i) in which one or plural amino acids are deleted, replaced or added in the amino acid sequence represented by SEQ ID NO: 1 or 3, and ii) which is an amino acid sequence of a protein capable of selectively hydrolyzing an ester moiety of either one enantiomer of the 2-alkyl-1,1,3-trialkoxycarbonylpropane; and e) an amino acid sequence i) having at least 90% homology to the amino acid sequence represented by SEQ ID NO: 1 or 3, and ii) which is an amino acid sequence of a protein capable of selectively hydrolyzing an ester moiety of either one enantiomer of the 2-alkyl-1,1,3-trialkoxycarbonylpropane.

MODE FOR CARRYING OUT THE INVENTION

In the following, the present invention will be explained in detail.

The 2-alkyl-1,1,3-trialkoxycarbonylpropane represented by Formula (1) (hereinafter, simply denoted by 2-alkyl-1,1, 3-trialkoxycarbonylpropane (1)) which is a material used in the process of the present invention can be produced in any known method such as a method of a reaction of dialkyl malonate and β-alkyl-α,β-unsaturated alkyl ester in the presence of a base (for example, see Tetrahedron, 44, 119 (1988)), and used in the present invention.

Typical examples of C1-C4 alkyl group represented by $R_1$, $R_2$ and $R_3$ in the compounds represented by the formulas (1) and (2) of the present invention include a methyl group, an ethyl group, an n-propyl group, an isopropyl group, an n-butyl group, an isobutyl group, a sec-butyl group, and a tert-butyl group.

Typical examples of the 2-alkyl-1,1,3-trialkoxycarbonylpropane (1) include 2-methyl-1,1,3-trimethoxycarbonylpropane, 2-methyl-1,1,3-triethoxycarbonylpropane, 2-methyl-1,1,3-tri-n-propoxycarbonylpropane, 2-ethyl-1,1,3-trimethoxycarbonylpropane, 2-ethyl-1,1,3-triethoxycarbonylpropane, 2-n-propyl-1,1,3-trimethoxycarbonylpropane, 2-n-propyl-1,1,3-triethoxycarbonylpropane, 2-methyl-1,1-diethoxycarbonyl-3-methoxycarbonylpropane, 2-methyl-1,1-di-n-propoxycarbonyl-3-methoxycarbonylpropane, 2-ethyl-1,1-diethoxycarbonyl-3-methoxycarbonylpropane, 2-ethyl-1,1-di-n-propoxycarbonyl-3-methoxycarbonylpropane, 2-n-propyl-1,1-diethoxycarbonyl-3-methoxycarbonylpropane, 2-methyl-1,1-dimethoxycarbonyl-3-ethoxycarbonylpropane, 2-methyl-1,1-di-n-propoxycarbonyl-3-ethoxycarbonylpropane, 2-ethyl-1,1-dimethoxycarbonyl-3-ethoxycarbonylpropane and 2-n-propyl-1,1-dimethoxycarbonyl-3-ethoxycarbonylpropane.

Examples of the enzyme capable of selectively hydrolyzing an ester moiety of an S isomer of 2-alkyl-1,1,3-trialkoxycarbonylpropane (1) include an enzyme originated from a microorganism of Candida such as Candida cylindracea and Candida rugosa, a microorganism of Chromobacterium chocolatum, pig liver and a thermophilic microorganism. The enzyme from a microorganism of Candida such as Candida cylindracea and Candida rugosa, a microorganism of Chromobacterium chocolatum and a thermophilic microorganism are preferred.

More specific examples of the enzyme capable of selectively hydrolyzing an ester moiety of an S isomer of the 2-alkyl-1,1,3-trialkoxycarbonylpropane (1) include an enzyme originated from Chromobacterium strain SC-YM-1 (FERM BP-6703) and commercially available enzymes CHIRAZYME (registered trademark) E-3 (originated from thermophilic microorganism), lipase CHIRAZYME (registered trademark) L-3 (originated from Candida rugosa), cholesterol esterase (originated from Candida cylindracea) (the above-mentioned are produced by Roche Diagnostics), lipase ChiroCLEC-CR (produced by Altus Biologics), lipase Lipase-MY (produced by Candida cylindracea) (produced by Meito Sangyo Co., Ltd.), and lipase Lipase OF (produced by Meito Sangyo Co., Ltd.) and PLE-A (produced by Amano Enzyme Inc.). The enzyme originated from Chromobacterium strain SC-YM-1 (FERM BP-6703) is more preferred.

Examples of the enzyme capable of selectively hydrolyzing an ester moiety of an R isomer of the 2-alkyl-1,1,3-trialkoxycarbonylpropane (1) include an enzyme originated from a microorganism of Bacillus such as Bacillus licheniformis and Bacillus subtilis, a microorganism of Arthrobacter globiformis, a microorganism of Candida antactica, bovine pancreas and a thermophilic microorganism. The enzyme originated from a microorganism of Bacillus such as Bacillus licheniformis and Bacillus subtilis, a microorganism of Arthrobacter globiformis, and a thermophilic microorganism are preferred.

More specific examples of the enzyme capable of selectively hydrolyzing an ester moiety of an R isomer of the 2-alkyl-1,1,3-trialkoxycarbonylpropane (1) include an enzyme originated from Arthrobacter strain SC-6-98-28 (FERM BP-3658), and commercially available enzymes such as esterase CHIRAZYME (registered trademark) E-4 (originated from thermophilic microorganism), protease CHIRAZYME (registered trademark) P-1 (originated from Bacillus licheniformis) (the above-mentioned are produced by Roche Diagnostics), protease Purafect (registered trademark) 4000E (produced by GENENCOR), protease α-Chymotrypsin (produced by SIGMA), and lipase SP-525 (produced by Novozymes Japan). The enzyme originated from Arthrobacter strain SC-6-98-28 (FERM BP-3658) is more preferred.

The enzyme capable of selectively hydrolyzing an ester moiety of either one of enantiomers of the 2-alkyl-1,1,3-trialkoxycarbonylpropane (1) (hereinafter, referred to as the present enzyme) may be enzymes originated from mutants induced by a treatment of these microorganisms with a mutagenic agent, ultraviolet rays or the like, enzymes produced by a recombinant microorganism transformed with a gene encoding the present enzyme possessed by these microorganisms, or mutated enzymes in which one or several amino acids in the present enzyme mentioned above are deleted, added, or replaced by genetic engineering technique in the process of the present invention as far as they are capable of selectively hydrolyzing an ester moiety of either one enantiomer of the 2-alkyl-1,1,3-trialkoxycarbonylpropane (1).

A recombinant microorganism transformed with a gene encoding the present enzyme can be prepared, for example, by an ordinary genetic engineering technique described, for example, in Molecular Cloning 2nd edition (written by J. Sambrook, E. F. Fritsch, and T. Maniatis, published by Cold Spring Harbor Laboratory, 1989) or similar methods. In addition, it can be prepared according to the methods described in JP2001-46084A, JP3855329, JP3875283, or JP3151893, or similar methods. Examples of the present enzyme produced by a recombinant microorganism that can be prepared in such a manner as described above include an esterase originated from Chromobacterium strain SC-YM-1 (FERM BP-6703) (JP3875283) or an esterase originated from Arthrobacter strain SC-6-98-28 (FERM BP-3658) (JP3151893).

A typical example of the esterase originated from Chromobacterium strain SC-YM-1 (FERM BP-6703) is an enzyme having an amino acid sequence represented by SEQ ID NO: 1, and a typical example of the esterase originated from Arthrobacter strain SC-6-98-28 (FERN BP-3658) is an enzyme having an amino acid sequence represented by SEQ ID NO: 3.

In the gene that encodes the present enzyme, for example, DNA having a nucleotide sequence represented by SEQ ID NO: 2 is a gene encoding the esterase originated from Chromobacterium strain SC-YM-1 (FERM BP-6703), and for example, DNA having a nucleotide sequence represented by SEQ ID NO: 4 is a gene encoding the esterase originated from Arthrobacter strain SC-6-98-28 (FERM BP-3658).

In the present invention, it is preferred to use an enzyme made of a protein having an amino acid sequence of either one of the following a) to e):
a) an amino acid sequence represented by SEQ ID NO: 1 or 3;
b) an amino acid sequence i) which is encoded by a nucleotide sequence of DNA having at least 90% homology to DNA having a nucleotide sequence represented by SEQ ID NO: 2 or 4, and ii) which is an amino acid sequence of a protein capable of selectively hydrolyzing an ester moiety of either one enantiomer of the 2-alkyl-1,1,3-trialkoxycarbonylpropane;
c) an amino acid sequence i) which is encoded by a nucleotide sequence of DNA that hybridizes with DNA having a nucleotide sequence represented by SEQ ID NO: 2 or 4 under a stringent condition, and ii) which is an amino acid sequence of a protein capable of selectively hydrolyzing an ester moiety of either one enantiomer of the 2-alkyl-1,1,3-trialkoxycarbonylpropane;
d) an amino acid sequence i) in which one or plural amino acids are deleted, replaced or added in the amino acid sequence represented by SEQ ID NO: 1 or 3, and ii) which is an amino acid sequence of a protein capable of selectively hydrolyzing an ester moiety of either one enantiomer of the 2-alkyl-1,1,3-trialkoxycarbonylpropane; and
e) an amino acid sequence i) having at least 90% homology to the amino acid sequence represented by SEQ ID NO: 1 or 3, and ii) which is an amino acid sequence of a protein capable of selectively hydrolyzing an ester moiety of either one enantiomer of the 2-alkyl-1,1,3-trialkoxycarbonylpropane.

Among them, it is more preferred to use an enzyme made of a protein having an amino acid sequence represented by at least 1st to 362nd amino acids in the amino acid sequence represented by SEQ ID NO: 1 in which the 43rd N (asparagine) is replaced by S (serine) (N43SA363term described in JP2000-78988A), or having an amino acid sequence represented by at least 1st to the 362nd amino acids in the amino acid sequence represented by SEQ ID NO: 1 in which the 160th G (glycine) is replaced by S (serine) and the 189th G (glycine) is replaced by F (phenylalanine) (160S189F363term described in J P3486942).

"DNA that hybridizes with DNA having a nucleotide sequence represented by SEQ ID NO: 2 or 4 under a stringent condition" refers to such DNA that (1) can form a DNA-DNA hybrid with DNA having a nucleotide sequence encoding an amino acid sequence represented by SEQ ID NO: 1 by allowing hybridization at 65° C. under a high ion concentration [for example, 6×SSC (900 mM of sodium chloride, 90 mM of sodium citrate) can be mentioned], and (2) can keep the hybrid even after 30-minute incubation at 65° C. under a low ion concentration [for example, 0.1×SSC (15 mM of sodium chloride, 1.5 mM of sodium citrate) can be mentioned], in Southern hybridization method described, for example, in "Cloning and Sequencing" (supervised by Itaru Watanabe, edited by Masahiro Sugiura, 1989, published by Nosonbunka-sha). Specifically, for example, DNA having a nucleotide sequence encoding an amino acid sequence represented by SEQ ID NO: 1 or 3, DNA having a nucleotide sequence in which a certain base is deleted, replaced or added in a nucleotide sequence encoding an amino acid sequence represented by SEQ ID NO: 1 or 3, DNA having at least 90%, preferably at least 95% homology to DNA having a nucleotide sequence encoding an amino acid sequence represented by SEQ ID NO: 1 or 3, and the like are recited.

The above-mentioned DNA may be DNA cloned from naturally occurring DNA, or DNA in which a certain base is artificially deleted, replaced or added in a nucleotide sequence of such cloned DNA, or artificially synthesized DNA. The homology can be calculated by using a sequence analyzing tool such as BESTFIT program supplied, for example, from UWGCG Package (Devereux et al (1984) Nucleic Acids Research 12, p387-395), PILEUP and BLAST algorism (Altschul S. F. (1993) J. Mol Evol 36: 290-300; Altschul S. F. (1990) J. Mol Biol 215: 403-10).

"The amino acid sequence in which one or plural amino acids are deleted, replaced or added in an amino acid sequence represented by SEQ ID NO: 1 or 3" is preferably an amino acid sequence in which one amino acid or two amino acids is/are deleted, replaced or added in an amino acid sequence represented by SEQ ID NO: 1 or 3. In addition, examples of the present enzyme include an amino acid sequence having at least 90%, preferably at least 95% homology to an amino acid sequence represented by SEQ ID NO: 1 or 2.

Microorganisms which produce the present enzyme can be liquid-cultured in any ordinary method. Various culture media appropriately containing a carbon source, a nitrogen source, an inorganic substance and the like used in ordinary microorganism culture can be used for the culture medium. For example, glucose, glycerin, organic acid and molasses can be used for the carbon source; peptone, yeast extract, malt extract, soy powder, corn steep liquor, cotton seed powder, dry yeast, casamino acid, ammonium chloride, ammonium nitrate, ammonium sulfate and urea can be used for the nitrogen source; and salts, sulfates, and phosphates of potassium, sodium, magnesium, iron, manganese, cobalt, zinc and the like, specifically, potassium chloride, sodium chloride, magnesium sulfate, ferrous sulfate, manganese sulfate, cobalt chloride, zinc sulfate, potassium phosphate, sodium phosphate and the like can be used for the inorganic substance. For improving the asymmetric hydrolyzing ability of the 2-alkyl-1,1,3-trialkoxycarbonylpropane (1) possessed by the aforementioned microorganism, triglyceride such as olive oil or tributyrin or the 2-alkyl-1,1,3-trialkoxycarbonylpropane (1) may be added appropriately to the culture medium.

In the case of a transformant formed by introducing a plasmid in which DNA encoding the present enzyme is downstream connected with a promoter of the type that is induced by allolactose such as tac promoter, trc promoter and lac promoter, for example, a small amount of isopropyl thio-β-D-galactoside (IPTG) can be added into a culture medium as an inducer for inducing production of the protein of the present invention.

In general, culture is preferably conducted aerobically, and shaking culture or culture under aeration and stirring is appropriate. Culture temperature is about 20 to 40° C., and preferably about 25 to 35° C., and pH is preferably about 6 to 8. Culture time is preferably about 1 to 7 days, though it varies depending on various conditions.

A solid culture method may also be appropriately employed, if required, as far as bacterial cells capable of asymmetrically hydrolyzing the 2-alkyl-1,1,3-trialkoxycarbonylpropane (1) can be obtained.

Purification of the present enzyme from a microbial culture obtained in the above manner may be conducted in a method ordinarily used in purification of enzyme. For example, bacterial cells in the microbial culture are disrupted by a method such as an ultrasonic treatment, a Dyno mill treatment, or a French press treatment at first. After removing insoluble materials from the obtained disrupted solution by centrifugation or the like, an objective enzyme can be purified by either one or combination of cation-exchange column chromatography, anion-exchange column chromatography, hydrophobic column chromatography, gel filtration column chromatography and the like that are ordinarily used in purification of enzyme. Examples of carriers usable in these column chromatographies include DEAE-Sepharose (registered trademark), fastflow (produced by GE Healthcare Bioscience) and Butyl-Toyopearl (registered trademark) 650S (produced by TOSOH Corporation).

The present enzyme can be used in various forms including a purified enzyme, a crude enzyme, a microbial culture, a bacterial cell, and a treated object thereof. Examples of the treated object used herein include a lyophilized bacterial cell, an acetone-dried bacterial cell, a ground bacterial cell, an autodigested substance of bacterial cell, an ultrasonic-treated object of bacterial cell, bacterial cell extract, or an alkaline-treated object of bacterial cell. Further, enzymes in various purities or forms as described above may be immobilized for use, for example, by known methods including an adsorption method to an inorganic carrier such as silica gel and ceramics, cellulose, ion-exchange resin and so on, a polyacrylamide method, a sulfur-containing polysaccharide gel method (for example, a carrageenan gel method), an alginic acid gel method, an agar gel method and so on.

A used amount of the present enzyme is appropriately determined so that delay of reaction time or decrease in selectivity will not occur, and for example, when a purified enzyme, a crude enzyme or a commercially available enzyme is used, the amount is usually 0.001 to 2 times by weight, preferably 0.002 to 0.5 time by weight, relative to that of the 2-alkyl-1,1,3-trialkoxycarbonylpropane (1), and when a microbial culture, a bacterial cell or a treated object thereof is used, the amount is usually 0.01 to 200 times by weight, preferably 0.1 to 50 times by weight, relative to that of the 2-alkyl-1,1,3-trialkoxycarbonylpropane (1).

Water used in the asymmetrical hydrolysis reaction may be a buffered aqueous solution. Examples of the buffered aqueous solution include buffered aqueous solutions of inorganic acid salt such as aqueous alkali phosphate solutions such as an aqueous sodium phosphate solution and an aqueous potassium phosphate solution, and buffered aqueous solutions of organic acid salt such as aqueous alkali acetate solutions such as an aqueous sodium acetate solution and an aqueous potassium acetate solution. A used amount of such water may be usually 0.5 time by mol or more, occasionally a solvent amount, and usually 200 times by weight or less, relative to that of the 2-alkyl-1,1,3-trialkoxycarbonylpropane (1).

Asymmetric hydrolysis reaction may be conducted in the presence of an organic solvent such as a hydrophobic organic solvent or a hydrophilic organic solvent. Examples of the hydrophobic organic solvent include ethers such as tert-butyl methyl ether and isopropyl ether, hydrocarbons such as toluene, hexane, cyclohexane, heptane, octane and isooctane, and examples of the hydrophilic organic solvent alcohols such as tert-butanol, methanol, ethanol, isopropanol, isobutanol and n-butanol, ethers such as tetrahydrofuran, sulfoxides such as dimethyl sulfoxide, ketones such as acetone, nitriles such as acetonitrile, amides such as N,N-dimethylformamide. These hydrophobic organic solvents and hydrophilic organic solvents are respectively used alone or in combination of two or more kinds, and a combination of hydrophobic organic solvent and hydrophilic organic solvent may be used.

When the organic solvent is used, a used amount thereof is usually 200 times by weight or less, preferably in the range of about 0.1 to 100 times by weight, relative to that of the 2-alkyl-1,1,3-trialkoxycarbonylpropane (1).

Asymmetric hydrolysis reaction is conducted, for example, by mixing water, the 2-alkyl-1,1,3-trialkoxycarbonylpropane (1) and the present enzyme, and when an organic solvent is used, the organic solvent, water, the 2-alkyl-1,1,3-trialkoxylcarbonylpropane (1) and the present enzyme may be mixed.

The pH value of the reaction system, at which asymmetric hydrolysis by the present enzyme proceeds with high selectivity, is appropriately selected, and is usually about pH 4 to 10, and preferably about pH 6 to 8, though it is not limited. The pH may be adjusted to a value in the selected range appropriately by adding a base during the reaction. Examples of the base include alkali hydroxides such as sodium hydroxide and potassium hydroxide, of alkali and alkaline earth carbonates such as sodium carbonate, potassium carbonate and calcium carbonate, alkali bicarbonates such as sodium bicarbonate and potassium bicarbonate, phosphates such as sodium dihydrogen phosphate, disodium hydrogen phosphate, potassium dihydrogen phosphate, and dipotassium hydrogen phosphate, organic bases such as triethyl amine and pyridine, and ammonia. The bases may be used alone or in combination of two or more kinds. While the base is usually used in an aqueous solution, it may be used in an organic solvent or a mixed solution of organic solvent and water when an organic solvent is used in the reaction. The organic solvent may be the same as that used in the reaction. Further, the base may be used in solid or in the state of being suspended in a solution.

A reaction temperature at which asymmetric hydrolysis by the present enzyme proceeds with high selectivity is appropriately selected. Though the temperature is not limited, too high temperature tends to reduce the stability of the enzyme and too low temperature tends to decrease the reaction speed. On the other hand, the lower the temperature the more the selectivity increases. It is usually in the range of about −10 to 65° C., preferably about −5 to 50° C.

Thus a solution of an optically active 2-alkyl-1,1,3-trialkoxycarbonylpropane represented by the formula (2) (hereinafter, simply referred to as optically active 2-alkyl- 1,1,3-trialkoxycarbonylpropane (2)) is obtained, and usually, a post treatment operation is further conducted for separation from the enzyme and the buffer used in the reaction, and the carboxylic acid generated by hydrolysis reaction.

Examples of the post treatment include a method of conducting separation and purification using silica gel chromatography after distilling off the solvent in the reaction solution, and a method of conducting separation and purification by distillation after distilling off the solvent, and a method of conducting separation and purification by liquid separation operation.

Separation and purification by liquid separation operation may be conducted after removing an organic solvent soluble in both water and a hydrophobic organic solvent may be removed by distillation when such an organic solvent is used in the reaction. When there are an insoluble enzyme, an immobilizing carrier and so on in the solution, these may be removed by filtration.

For separating the optically active 2-alkyl-1,1,3-trialkoxycarbonylpropane (2) which is an objective substance from the enzyme, the buffer and other water-soluble components, a hydrophobic organic solvent may be used for extracting the optically active 2-alkyl-1,1,3-trialkoxycarbonylpropane (2) with an organic phase, and the organic phase may be separated from an aqueous phase.

Examples of the hydrophobic organic solvent include ethers such as tert-butyl methyl ether and isopropyl ether, hydrocarbons such as toluene, hexane, cyclohexane, heptane, octane and isooctane, halogenated hydrocarbons such as dichloromethane, dichloroethane, chloroform, chlorobenzene and orthodichlorobenzene, and esters such as ethyl acetate, methyl acetate and butyl acetate. When the hydrophobic organic solvent is used in the reaction, the liquid separation operation may be conducted directly. Alternatively, when the hydrophobic organic solvent is not used in the reaction, or when the liquid separation can not be achieved due to the small amount used, or when the liquid separation cannot be readily achieved due to the small amount of the used water, the hydrophobic organic solvent, water and the like may be appropriately added before the liquid separation. A used amount of the hydrophobic organic solvent is usually 0.1 to 200 times by weight, and preferably in the range of about 0.2 to 100 times by weight, relative to that of the 2-alkyl-1,1,3-trialkoxycarbonylpropane (1), though it is not limited.

The pH in the extraction of the objective substance is usually in the range of about 6 to 10, and preferably in the range of about 7 to 9.

For adjusting the pH of the solution into the range, an acid or a base may be appropriately used. Examples of the acid include inorganic acids such as hydrogen chloride, hydrogen bromide, sulfuric acid and phosphoric acid and salts thereof, and bases thereof, and organic acids such as acetic acid, citric acid and methanesulfonic acid, and salts thereof. A base similar to that used for adjusting pH in the reaction may be used.

When extraction of the objective substance from the aqueous phase is insufficient, the same extraction and liquid separation operation may be repeated plural times. Likewise, when removal of the water-soluble components from the organic phase is insufficient, the same extraction and liquid separation operation may be repeated plural times Next, by distilling off the organic solvent in the obtained organic phase, the optically active 2-alkyl-1,1,3-trialkoxycarbonylpropane (2) which is an objective substance can be isolated.

The obtained optically active 2-alkyl-1,1,3-trialkoxycarbonylpropane (2) may further be purified by column chromatography or distillation.

In the present invention, when an enzyme capable of selectively hydrolyzing an ester moiety of an S isomer of the 2-alkyl-1,1,3-trialkoxycarbonylpropane (1) is used for the present enzyme, the optically active 2-alkyl-1,1,3-trialkoxycarbonylpropane (2) obtained from the organic phase in the liquid separation treatment is rich in R isomer, while when an enzyme capable of selectively hydrolyzing an ester moiety of an R isomer of the 2-alkyl-1,1,3-trialkoxycarbonylpropane (1) is used for the present enzyme, the optically active 2-alkyl-1,1,3-trialkoxycarbonylpropane (2) obtained from the organic phase in the liquid separation treatment is rich in S isomer.

The aqueous phase after the liquid separation operation usually contains a hydrolysis product having opposite stereoisomerism to that of the objective substance obtained from the organic phase. In other words, when an enzyme capable of selectively hydrolyzing an ester moiety of an S isomer is used, the aqueous phase contains a hydrolysis product of the optically active (S)-2-alkyl-1,1,3-trialkoxycarbonylpropane, and when an enzyme capable of selectively hydrolyzing an ester moiety of an R isomer is used, the aqueous phase contains a hydrolysis product of the optically active (R)-2-alkyl-1,1,3-trialkoxycarbonylpropane. These hydrolysis products may be collected by distilling off water from the aqueous phase, or by extracting the aqueous phase with an organic solvent after adjusting the aqueous phase to acidic, and concentrating the obtained organic phase. By esterifying the obtained hydrolysis product, the corresponding optically active 2-alkyl-1,1,3-trialkoxycarbonylpropane (2) can be obtained. Such esterification may be conducted by conventional methods, for example, a method of reacting the hydrolysis product with alcohol in the presence of sulfuric acid; a method of reacting the hydrolysis product with alcohol in the presence of trimethylsilyl azide or trimethylsilyl chloride.

Examples of the typical optically active 2-alkyl-1,1,3-trialkoxycarbonylpropane (2) thus obtained include (R)-2-methyl-1,1,3-trimethoxycarbonylpropane, (R)-2-methyl-1,1,3-triethoxycarbonylpropane, (R)-2-methyl-1,1,3-tri-n-propoxycarbonylpropane, (R)-2-ethyl-1,1,3-trimethoxycarbonylpropane, (R)-2-ethyl-1,1,3-triethoxycarbonylpropane, (R)-2-n-propyl-1,1,3-trimethoxycarbonylpropane, (R)-2-n-propyl-1,1,3-triethoxycarbonylpropane, (R)-2-methyl-1,1-diethoxycarbonyl-3-methoxcarbonylpropane, (R)-2-methyl-1,1-di-n-propoxycarbonyl-3-methoxycarbonylpropane, (R)-2-ethyl-1,1-diethoxycarbonyl-3-methoxycarbonylpropane, (R)-2-ethyl-1,1-di-n-propoxycarbonyl-3-methoxycarbonylpropane, (R)-2-n-propyl-1,1-diethoxycarbonyl-3-methoxycarbonylpropane, (R)-2-methyl-1,1-dimethoxycarbonyl-3-ethoxycarbonylpropane, (R)-2-methyl-1,1-di-n-propoxycarbonyl-3-ethoxycarbonylpropane, (R)-2-ethyl-1,1-dimethoxycarbonyl-3-ethoxycarbonylpropane, (R)-2-n-propyl-1,1-dimethoxycarbonyl-3-ethoxycarbonylpropane, and compounds wherein (R) is replaced by (S).

EXAMPLES

In the following, the present invention will be explained more specifically by way of examples; however, the present invention is not limited to these examples.

Examples 1 to 14

To 35 mg of 2-methyl-1,1,3-trimethoxycarbonylpropane and each of various enzymes shown in Table 1 respectively weighed in the amount shown in Table 2, 2 mL of 100 mM potassium phosphate buffer (pH 7.0) was added. The resultant solution was stirred at 25° C. for 20 hours, and then 2.5 mL of acetonitrile was added thereto and the mixture was drawn through a membrane filter. The optical purity of the resultant filtrate was analyzed by high performance liquid chromatography [column: CHIRALCEL (registered trademark) OB-H, 4.6 mmφ×15 cm, 5 µm (produced by Daicel Chemical Industries, Ltd.)], and the chemical purity was analyzed by high performance liquid chromatography [column: SUMIPAX ODS D-21OFF, 4.6 mmφ×15 cm, 3 µm (available from Sumika Chemical Analysis Service, Ltd.)]; and thus, yield and enantiomer excess of the obtained optically active 2-methyl-1,1,3-trimethoxycarbonylpropane were determined. The results are shown in Table 2.

Examples 15, 16

To 70 mg of 2-methyl-1,1,3-trimethoxycarbonylpropane and an enzyme shown in Table 1 weighed in the amount shown in Table 2, 4 mL of 100 mM potassium phosphate buffer (pH 7.0) was added. The resultant solution was stirred at 25° C. for 3.5 hours, and then 5 mL of acetonitrile was added thereto and the mixture was drawn through a membrane filter. The filtrate was analyzed in the same method as in Examples 1 to 14, and yield and enantiomer excess of obtained optically active 2-methyl-1,1,3-trimethoxycarbonylpropane were determined. The results are shown in Table 2.

TABLE 2

| Example | Amount of enzyme (mg) | Yield (%) | Enantiomer excess (% ee) | Excess optical isomer |
|---|---|---|---|---|
| 1 | 2.2 | 9.6 | 100 | (R)-isomer |
| 2 | 2.1 | 9.6 | 100 | (R)-isomer |
| 3 | 2.1 | 5.6 | 100 | (R)-isomer |
| 4 | 2.1 | 2.8 | 100 | (R)-isomer |
| 5 | 2.0 | 24.4 | 51.5 | (R)-isomer |
| 6 | 2.0 | 77.0 | 7.3 | (R)-isomer |
| 7 | 2.2 | 61.3 | 18.7 | (R)-isomer |
| 8 | 2.4 | 77.5 | 8.2 | (R)-isomer |
| 9 | 74.8 | 14.4 | 100 | (S)-isomer |
| 10 | 2.0 | 46.9 | 46.5 | (S)-isomer |
| 11 | 2.1 | 53.0 | 36.3 | (S)-isomer |
| 12 | 10.2 | 62.6 | 31.3 | (S)-isomer |
| 13 | 1.4 | 53.8 | 14.0 | (S)-isomer |
| 14 | 2.1 | 71.2 | 6.6 | (S)-isomer |
| 15 | 7.0 | 37.5 | 95.0 | (R)-isomer |
| 16 | 7.0 | 36.5 | 96.5 | (R)-isomer |

Examples 17, 18

To 70 mg of 2-methyl-1,1,3-trimethoxycarbonylpropane and 7.0 mg of esterase derived from Chromobacterium strain SC-YM-1 (160S189F363term), 4 mL of 100 mM potassium phosphate buffer either at pH 5 or pH 9 was added. The resultant solution was stirred at 25° C. for 3.5 hours, and then 5 mL of acetonitrile was added thereto and the mixture was drawn through a membrane filter. The filtrate was analyzed in the same method as in Examples 1 to 14, and yield and enantiomer excess of the obtained

TABLE 1

| Example | Name of enzyme | Origin of enzyme | Enzyme manufacturer (commercially available enzyme) | Preparation method of enzyme |
|---|---|---|---|---|
| 1 | Cholesterol Esterase | *Candida cylindracea* | Roche Diagnostics | |
| 2 | CHIRAZYME E-3, lyo | Thermophilic micro-organism | Roche Diagnostics | |
| 3 | Cholesterol esterase, lyo | *Candida cylindracea* | Roche Diagnostics | |
| 4 | PLE-A | Pig liver | Amano Enzyme | |
| 5 | ChiroCLEC-CR | *Candida rugosa* | Altus Biologics | |
| 6 | CHIRAZYME L-3 | *Candida rugosa* | Roche Diagnostics | |
| 7 | Lipase OF | *Candida cylindracea* | Meito Sangyo | |
| 8 | Lipase-MY | *Candida cylindracea* | Meito Sangyo | |
| 9 | Esterase originated from Arthrobacter strain SC-6-98-28 | *Arthrobacter globiformis* | | Prepared according to the method described in JP 3151893 |
| 10 | CHIRAZYME E-4, Lyo. | Thermophilic micro-organism | Roche Diagnostics | |
| 11 | CHIRAZYME P-1, Lyo. (Subtilisin) | *Bacillus licheniformis* | Roche Diagnostics | |
| 12 | Purafect 4000E | *Bacillus subtilis* | GENENCOR | |
| 13 | SP-525 | *Candida antactica* | Novozymes Japan | |
| 14 | α-Chymotrypsin | Bovine pancreas | SIGMA | |
| 15 | Esterase 160S189F363term originated from Chromobacterium strain SC-YM-1 | *Chromobacterium chocolatum* | | Prepared according to the method described in JP 3486942 |
| 16 | Esterase 160A189Y363term originated from Chromobacterium strain SC-YM-1 | *Chromobacterium chocolatum* | | Prepared according to the method described in JP 3486942 | optically active 2-methyl-1,1,3-trimethoxycarbonylpropane were determined. The results compared with Example 15 (pH7) are shown in Table 3.

TABLE 3

| Example | pH | Yield (%) | Enantiomer excess (% ee) | Excess optical isomer |
|---|---|---|---|---|
| 17 | 9 | 36.2 | 100.0 | (R)-isomer |
| 15 | 7 | 37.5 | 95.0 | (R)-isomer |
| 18 | 5 | 78.0 | 21.0 | (R)-isomer |

Examples 19, 20

To 70 mg of 2-methyl-1,1,3-trimethoxycarbonylpropane and 7.0 mg of esterase derived from Chromobacterium strain SC-YM-1 (160S189F363term), 4 mL of 100 mM potassium phosphate buffer (pH7.0) was added. The resultant solution was stirred at 10° C. or 0° C. for a time described in Table 4, and then 5 mL of acetonitrile was added thereto and the mixture was drawn through a membrane filter. The filtrate was analyzed in the same method as in Examples 1 to 14, and yield and enantiomer excess of the obtained optically active 2-methyl-1,1,3-trimethoxycarbonylpropane were determined. The results compared with Example 15 (25° C.) are shown in Table 4.

TABLE 4

| Example | Temperature (° C.) | Time (hr) | Yield (%) | Enantiomer excess (% ee) | Excess optical isomer |
|---|---|---|---|---|---|
| 15 | 25 | 3.5 | 37.5 | 95.2 | (R)-isomer |
| 19 | 10 | 8.0 | 47.3 | 91.8 | (R)-isomer |
| 20 | 0 | 21.0 | 42.3 | 100.0 | (R)-isomer |

Examples 21-29

E. coli strain JM105 was transformed with a plasmid including each esterase gene shown in Table 5. The obtained transformant was inoculated onto sterile LB (1% Bacto-Triptone, 0.5% Bacto-Yeast extract, 1% sodium chloride) culture medium (100 ml) containing 0.1 mM IPTG and 50 µg/ml of ampicillin, and cultured under shaking (37° C., 24 hours). The obtained culture liquid was centrifuged, to obtain about 0.6 g of wet bacterial cells. About 0.6 g of wet bacterial cells were suspended in 5 mL of 0.1 M potassium phosphate buffer (pH 7.0), 5 g of glass beads of 0.1 mm in diameter was added, and then disrupted by a Multi-beads shocker (produced by Yasui Kikai Corporation, 2500 rpm, 20 minutes). The obtained disrupted liquid was centrifuged (10000 rpm, 4° C., 10 minutes), and the supernatant was provided as a crude enzyme liquid.

To 70 mg of 2-methyl-1,1,3-trimethoxycarbonylpropane, the crude enzyme liquid was added in the enzyme amount shown in Table 6, and further 4 mL of 170 mM potassium phosphate buffer (pH 7.0) was added. The solution was stirred at 25° C. for 5 hours, 2 mL of acetonitrile containing biphenyl (internal standard substance) was added thereto, and the mixture was drawn through a membrane filter. The filtrate was analyzed in the same method as in Examples 1 to 14, and yield and enantiomer excess of the obtained optically active 2-methyl-1,1,3-trimethoxycarbonylpropane were determined. The results are shown in Table 6.

TABLE 5

| Example | Name of enzyme | Origin of enzyme | Plasmid |
|---|---|---|---|
| 21 | Esterase N43SA363term originated from Chromobacterium strain SC-YM-1 | Chromobacterium chocolatum | pCCN43SA363term (see JP2000-78988A) |
| 22 | Esterase 160S189Y363term originated from Chromobacterium strain SC-YM-1 | Chromobacterium chocolatum | pCC160S189Y363term (see JP3486942) |
| 23 | Esterase 160A189H363term originated from Chromobacterium strain SC-YM-1 | Chromobacterium chocolatum | pCC160A189H363term (see JP3486942) |
| 24 | Esterase 160S189H363term originated from Chromobacterium strain SC-YM-1 | Chromobacterium chocolatum | pCC160S189H363term (see JP3486942) |
| 25 | Esterase 160A189F363term originated from Chromobacterium strain SC-YM-1 | Chromobacterium chocolatum | pCC160A189F363term (see JP3486942) |

TABLE 5-continued

| Example | Name of enzyme | Origin of enzyme | Plasmid |
|---|---|---|---|
| 26 | Esterase V325I originated from *Chromobacterium* strain SC-YM-1 | *Chromobacterium chocolatum* | pCCV325I (see JP2000-78988A) |
| 27 | Esterase originated from *Chromobacterium* strain SC-YM-1 | *Chromobacterium chocolatum* | pCC363term (see JP3486942) |
| 28 | Esterase 160A189Y363term originated from *Chromobacterium* strain SC-YM-1 | *Chromobacterium chocolatum* | pCC160A189Y363term (see JP3486942) |
| 29 | Esterase T240AV288A originated from *Chromobacterium* strain SC-YM-1 | *Chromobacterium chocolatum* | pCCT240AV288A (see JP2000-78988A) |

TABLE 6

| Example | Amount of enzyme (mg) | Yield (%) | Enantiomer excess (% ee) | Excess optical isomer |
|---|---|---|---|---|
| 21 | 34.6 | 40.9 | 100 | (R)-isomer |
| 22 | 34.9 | 18.1 | 100 | (R)-isomer |
| 23 | 35.3 | 23.8 | 100 | (R)-isomer |
| 24 | 35.3 | 10.9 | 100 | (R)-isomer |
| 25 | 35.2 | 6.2 | 100 | (R)-isomer |
| 26 | 34.6 | 9.5 | 100 | (R)-isomer |
| 27 | 34.7 | 20.9 | 100 | (R)-isomer |
| 28 | 34.9 | 12.2 | 100 | (R)-isomer |
| 29 | 35.1 | 6.3 | 100 | (R)-isomer |

Example 30-1

Enzymatic Hydrolysis

To 11.37 g of 2-methyl-1,1,3-trimethoxycarbonylpropane and 68.4 g of 100 mM potassium phosphate buffer (pH 7.0), 1.0 g of a crude enzyme liquid prepared in the same method as in Examples 21 to 29 from a transformant of E. coli strain JM105 containing plasmid (pCCN43SA363term) was added. The resultant solution was stirred at 0° C. for 23 hours. During stirring, pH of the solution was kept at 7 by dropping 10 wt % of aqueous sodium hydroxide solution. After stirring the solution, 20 g of tert-butyl methyl ether was added, and the obtained mixture was drawn through a glass filter. The filtrate was separated into an organic phase and an aqueous phase. To the aqueous phase, 20 g of tert-butyl methyl ether was added and a phase separation gave 81.8 g of an aqueous phase. The obtained organic phases were combined and washed with 5.1 g of 5 wt % of aqueous sodium bicarbonate solution. The washed organic phase was concentrated under reduced pressure, to obtain 4.49 g of (R)-2-methyl-1,1,3-trimethoxycarbonylpropane as a yellow oily substance. Yield: 47.7%, Enantiomer excess: 100% ee.

Example 30-2

Collection of Hydrolysate

To 79.8 g of the aqueous phase obtained in Example 30-1, 3.12 g of 35 wt % of hydrochloric acid was added to adjust pH at 2.0. After adding 20.0 g of ethyl acetate and 25.0 g of sodium chloride and stirring the same, the obtained mixture was subjected to liquid separation. 25.0 g of ethyl acetate was added to the obtained aqueous phase, and extracted. The obtained organic phases were combined and washed with 25.0 g of 25 wt % of aqueous sodium chloride solution. The washed organic phase was concentrated under reduced pressure to obtain 5.1 g of a yellow-brown oily substance.

Example 30-3

Esterification 1.0 g of the yellow-brown oily substance obtained in Example 30-2 was dissolved in 20.0 g of methanol. The obtained solution was cooled to 0° C., and 1.0 g of trimethylsilyl chloride was added dropwise over about 10 minutes. After dropping, temperature of the obtained reaction solution was raised to 20 to 25° C., and kept at this temperature for 45.5 hours. The obtained reaction solution was diluted with 32 g of tert-butyl methyl ether. After adding 40 g of 5 wt % of aqueous sodium bicarbonate solution and stirring the same, liquid separation was conducted to obtain 36.2 g of an organic phase and 57.8 g of an aqueous phase. For each of the obtained organic phase and aqueous phase, the chemical purity was analyzed by high performance liquid chromatography, and for the organic phase, the optical purity was analyzed by high performance liquid chromatography, and the yield and enantiomer excess of the obtained optically active 2-methyl1,1,3-trimethoxycarbonylpropane were determined. The chemical purity and the optical purity were analyzed in the same method as in Examples 1 to 14. Yield of 2-methyl-1,1,3-trimethoxycarbonylpropane contained in the organic phase and aqueous phase was 46.8%, and enantiomer excess of 2-methyl-1,1,3-trimethoxycarbonylpropane contained in the organic phase was 86.8% ee (S isomer).

Example 31-1

Enzymatic Hydrolysis

To 150 g of 2-methyl-1,1,3-trimethoxycarbonyl propane and 1035 g of 100 mM potassium phosphate buffer (pH 7.0), 17.0 g of a crude enzyme liquid prepared in the same method as in Examples 21 to 29 from a transformant of E. coli strain JM105 containing plasmid (pCC160S189F363term) was added. The resultant solution was stirred at 0° C. for 42 hours. During stirring, the pH of the solution was kept at 7 by dropping 10 wt % of aqueous sodium hydroxide solution. The solution after end of the stirring was added with 613 g of ethyl acetate, and the obtained mixture was drawn through a glass filter. The filtrate was separated into an organic phase and an aqueous phase, and the aqueous phase was separated by adding 750 g of ethyl acetate. The obtained organic phases were combined, to obtain 1500 g of an organic phase and 1321 g of an aqueous phase. The organic phase was further washed with 150 g of 5 wt % of aqueous sodium bicarbonate solution. The washed organic phase was concentrated under reduced pressure, to obtain 67.6 g of (R)-2-methyl-1,1,3-trimethoxycarbonylpropane as a yellow oily substance. Yield: 39.1%, Enantiomer excess: 100% ee.

Example 31-2

Collection of Hydrolysate

To 1315 g of the aqueous phase obtained in Example 31-1, 61 g of 35 wt % hydrochloric acid was added to adjust pH at 2.0. After adding 300 g of ethyl acetate and 415 g of sodium chloride and stirring the same, the obtained mixture was subjected to liquid separation. To the obtained aqueous phase, 375 g of ethyl acetate was added and extracted. The obtained organic phases were combined and washed with 375 g of 25 wt % of aqueous sodium chloride solution. The washed organic phase was concentrated under reduced pressure to obtain 105 g of a yellow-brown oily substance.

Example 31-3

Esterification 1.0 g of the yellow-brown oily substance obtained in Example 31-2 was dissolved in 20.1 g of methanol. The obtained solution was cooled to 0° C., and 1.0 g of trimethylsilyl chloride was added dropwise over about 10 minutes. After dropping, temperature of the obtained reaction solution was raised to 20 to 25° C., and kept at this temperature for 45 hours. The obtained reaction solution was diluted with 32 g of tert-butyl methyl ether. After adding 40 g of 5 wt % of aqueous sodium bicarbonate solution and stirring the same, liquid separation was conducted to obtain 37.0 g of an organic phase and 57.3 g of an aqueous phase. When analyzing in the same method as in Example 30-3, yield of 2-methyl-1,1,3-trimethoxycarbonylpropane contained in the organic phase and aqueous phase was 51.1%, and enantiomer excess of 2-methyl-1,1,3-trimethoxycarbonylpropane contained in the organic phase was 70.6% ee (S isomer).

Industrial Applicability

According to the method of the present invention, it is possible to produce an optically active 2-alkyl-1,1,3-trialkoxycarbonylpropane with high optical purity without using a low temperature condition.

The invention claimed is:

1. A process for producing an optically active 2-alkyl-1,1,3-trialkoxycarbonylpropane of Formula (2):

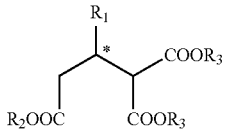

wherein:
R$_1$, R$_2$ and R$_3$, which may be the same or different, are a C1-C4 alkyl group; and
* represents an asymmetrical center; comprising hydrolyzing a 2-alkyl-1,1,3-trialokoxycarbonylpropane of Formula (1):

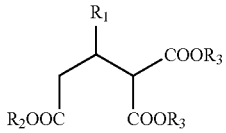

wherein R$_1$, R$_2$ and R$_3$ are as defined above,
by contacting the 2-alkyl-1,1,3-trialkoxycarbonylpropane represented by Formula (1) with a culture of a microorganism, wherein the microorganism comprises an enzyme capable of selectively hydrolyzing an ester moiety of either one enantiomer,
wherein the enzyme comprises the amino acid sequence of SEQ ID NO: 1 or SEQ ID NO: 3,
to provide the optically active 2-alkyl-1,1,3-trialkoxycarbonylpropane of Formula (2).

2. The process according to claim 1, wherein R$_1$ is methyl.

3. The process according to claim 1, wherein R$_2$ is methyl.

4. The process according to claim 1, wherein R$_3$ is methyl.

5. The process according to claim 1, wherein both R$_1$ and R$_2$ are methyl.

6. The process according to claim 1, wherein both R$_2$ and R$_3$ are methyl.

7. The process according to claim 1, wherein R$_1$, R$_2$ and R$_3$ are methyl.

8. The process according to claim 1, wherein the enzyme comprises the amino acid sequence of SEQ ID NO: 1.

9. The process according to claim 1, wherein the enzyme comprises the amino acid sequence of SEQ ID NO: 3.

* * * * *

SEQUENCE LISTING

```
<160> NUMBER OF SEQ ID NOS: 4

<210> SEQ ID NO 1
<211> LENGTH: 370
<212> TYPE: PRT
<213> ORGANISM: Chromobacterium chocolatum

<400> SEQUENCE: 1

Met Thr Leu Phe Asp Gly Ile Thr Ser Arg Ile Val Asp Thr Asp Arg
  1               5                  10                  15

Leu Thr Val Asn Ile Leu Glu Arg Ala Ala Asp Asp Pro Gln Thr Pro
                 20                  25                  30

Pro Asp Arg Thr Val Val Phe Val His Gly Asn Val Ser Ser Ala Leu
             35                  40                  45

Phe Trp Gln Glu Ile Met Gln Asp Leu Pro Ser Asp Leu Arg Ala Ile
 50                  55                  60

Ala Val Asp Leu Arg Gly Phe Gly Gly Ser Glu His Ala Pro Val Asp
 65                  70                  75                  80

Ala Thr Arg Gly Val Arg Asp Phe Ser Asp Asp Leu His Ala Thr Leu
                 85                  90                  95

Glu Ala Leu Asp Ile Pro Val Ala His Leu Val Gly Trp Ser Met Gly
            100                 105                 110

Gly Gly Val Val Met Gln Tyr Ala Leu Asp His Pro Val Leu Ser Leu
            115                 120                 125

Thr Leu Gln Ser Pro Val Ser Pro Tyr Gly Phe Gly Gly Thr Arg Arg
130                 135                 140

Asp Gly Ser Arg Leu Thr Asp Asp Ala Gly Cys Gly Gly Gly Gly
145                 150                 155                 160

Ala Asn Pro Asp Phe Ile Gln Arg Leu Ile Asp His Asp Thr Ser Asp
                165                 170                 175

Asp Ala Gln Thr Ser Pro Arg Ser Val Phe Arg Ala Gly Tyr Val Ala
```

```
                    180                 185                 190
Ser Asp Tyr Thr Thr Asp His Glu Asp Val Trp Val Glu Ser Met Leu
                195                 200                 205

Thr Thr Ser Thr Ala Asp Gly Asn Tyr Pro Gly Asp Ala Val Pro Ser
            210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
                245                 250                 255

Lys Pro Pro Ile Leu Trp Ile His Gly Thr Ala Asp Ala Ile Val Ser
            260                 265                 270

Asp Ala Ser Phe Tyr Asp Leu Asn Tyr Leu Gly Gln Leu Gly Ile Val
                275                 280                 285

Pro Gly Trp Pro Gly Glu Asp Val Ala Pro Ala Gln Glu Met Val Ser
                290                 295                 300

Gln Thr Arg Asp Val Leu Gly Arg Tyr Ala Ala Gly Gly Thr Val
305                 310                 315                 320

Thr Glu Val Ala Val Glu Gly Ala Gly His Ser Ala His Leu Glu Arg
                325                 330                 335

Pro Ala Val Phe Arg His Ala Leu Leu Glu Ile Ile Gly Tyr Val Gly
                340                 345                 350

Ala Ala Ala Asp Pro Ala Pro Pro Thr Glu Ala Ile Ile Ile Arg Ser
            355                 360                 365

Ala Asp
    370

<210> SEQ ID NO 2
<211> LENGTH: 1110
<212> TYPE: DNA
<213> ORGANISM: Chromobacterium chocolatum
<220> FEATURE:
<221> NAME/KEY: CDS
<222> LOCATION: (1)..(1110)

<400> SEQUENCE: 2 atg acc ctg ttc gac ggc atc acg tct cgc atc gtc gac acc gac cgc       48
Met Thr Leu Phe Asp Gly Ile Thr Ser Arg Ile Val Asp Thr Asp Arg
1               5                   10                  15 ctg acc gtg aac atc ctg gag cgc gcg gcc gac gac ccg cag acc ccg       96
Leu Thr Val Asn Ile Leu Glu Arg Ala Ala Asp Asp Pro Gln Thr Pro
                20                  25                  30 ccc gac cgc acg gtc gtg ttc gtc cac ggg aat gtg tcc tcc gcg ctg      144
Pro Asp Arg Thr Val Val Phe Val His Gly Asn Val Ser Ser Ala Leu
            35                  40                  45 ttc tgg cag gag atc atg cag gac ctg ccg agc gac ctg cgc gcc atc      192
Phe Trp Gln Glu Ile Met Gln Asp Leu Pro Ser Asp Leu Arg Ala Ile
        50                  55                  60 gcg gtc gac ctg cgc ggc ttc ggc ggc tcg gag cac gcg ccg gtc gac      240
Ala Val Asp Leu Arg Gly Phe Gly Gly Ser Glu His Ala Pro Val Asp
65                  70                  75                  80 gcc acc cgc ggc gtc cgc gac ttc agc gac gat ctg cac gcg acc ctc      288
Ala Thr Arg Gly Val Arg Asp Phe Ser Asp Asp Leu His Ala Thr Leu
                85                  90                  95 gag gcg ctc gac atc ccg gtc gcg cat ctg gtc ggc tgg tcg atg ggc      336
Glu Ala Leu Asp Ile Pro Val Ala His Leu Val Gly Trp Ser Met Gly
            100                 105                 110 ggc ggc gtc gtc atg cag tat gcc ctc gac cac ccg gtg ctg agc ctg      384
Gly Gly Val Val Met Gln Tyr Ala Leu Asp His Pro Val Leu Ser Leu
```

```
                 115                 120                 125
acc ctg cag tcg ccg gtg tcg ccc tac ggc ttc ggc ggc acc cgc cgt      432
Thr Leu Gln Ser Pro Val Ser Pro Tyr Gly Phe Gly Gly Thr Arg Arg
    130                 135                 140 gac ggc tca cgc ctc acc gac gac gat gcc ggc tgc ggt ggc ggc ggt      480
Asp Gly Ser Arg Leu Thr Asp Asp Asp Ala Gly Cys Gly Gly Gly Gly
145                 150                 155                 160 gcg aac ccc gac ttc atc cag cgc ctc atc gac cac gac acc tcc gac      528
Ala Asn Pro Asp Phe Ile Gln Arg Leu Ile Asp His Asp Thr Ser Asp
                165                 170                 175 gat gcg cag acc tcg ccc cgg agc gtc ttc cgc gcc ggc tac gtc gcc      576
Asp Ala Gln Thr Ser Pro Arg Ser Val Phe Arg Ala Gly Tyr Val Ala
            180                 185                 190 tcg gac tac acc acc gac cac gag gac gtg tgg gtc gaa tcg atg ctc      624
Ser Asp Tyr Thr Thr Asp His Glu Asp Val Trp Val Glu Ser Met Leu
        195                 200                 205 acc acg tcc acc gcc gac gga aac tac ccc ggc gat gcg gtg ccg agc      672
Thr Thr Ser Thr Ala Asp Gly Asn Tyr Pro Gly Asp Ala Val Pro Ser
    210                 215                 220 gac aac tgg ccg ggc ttc gcc gcc ggc cgc cac ggc gtg ctg aac acc      720
Asp Asn Trp Pro Gly Phe Ala Ala Gly Arg His Gly Val Leu Asn Thr
225                 230                 235                 240 atg gcc ccg cag tac ttc gat gtg tcg ggg att gtc gac ctg gcc gag      768
Met Ala Pro Gln Tyr Phe Asp Val Ser Gly Ile Val Asp Leu Ala Glu
                245                 250                 255 aag cct ccg atc ctg tgg atc cac ggc acc gcg gac gcg atc gtc tcc      816
Lys Pro Pro Ile Leu Trp Ile His Gly Thr Ala Asp Ala Ile Val Ser
            260                 265                 270 gac gcg tcg ttc tac gac ctc aac tac ctc ggc cag ctg ggc atc gtc      864
Asp Ala Ser Phe Tyr Asp Leu Asn Tyr Leu Gly Gln Leu Gly Ile Val
        275                 280                 285 ccc ggc tgg ccc ggc gaa gac gtc gcg ccc gcg cag gag atg gtg tcg      912
Pro Gly Trp Pro Gly Glu Asp Val Ala Pro Ala Gln Glu Met Val Ser
    290                 295                 300 cag acc cgc gat gtc ctc ggc cgc tac gct gcg ggc ggc gga acg gtc      960
Gln Thr Arg Asp Val Leu Gly Arg Tyr Ala Ala Gly Gly Gly Thr Val
305                 310                 315                 320 acc gag gtc gcc gtc gag ggc gcg ggc cac tcc gcg cac ctg gag cgt     1008
Thr Glu Val Ala Val Glu Gly Ala Gly His Ser Ala His Leu Glu Arg
                325                 330                 335 ccc gcg gtg ttc cgc cac gcg ctg ctc gag atc atc ggc tac gtc ggc     1056
Pro Ala Val Phe Arg His Ala Leu Leu Glu Ile Ile Gly Tyr Val Gly
            340                 345                 350 gcg gcg gcc gac ccc gcc ccg ccg acc gag gcg atc atc atc cgc tcc     1104
Ala Ala Ala Asp Pro Ala Pro Pro Thr Glu Ala Ile Ile Ile Arg Ser
        355                 360                 365 gcc gac                                                              1110
Ala Asp
    370

<210> SEQ ID NO 3
<211> LENGTH: 375
<212> TYPE: PRT
<213> ORGANISM: Arthrobacter globiformis

<400> SEQUENCE: 3

Met Asp Ala Gln Thr Ile Ala Pro Gly Phe Glu Ser Val Ala Glu Leu
 1               5                  10                  15

Phe Gly Arg Phe Leu Ser Glu Asp Arg Glu Tyr Ser Ala Gln Leu Ala
            20                  25                  30
```

Ala Tyr His Arg Gly Val Lys Val Leu Asp Ile Ser Gly Gly Pro His
         35                  40                  45

Arg Arg Pro Asp Ser Val Thr Gly Val Phe Ser Cys Ser Lys Gly Val
 50                  55                  60

Ser Gly Leu Val Ile Ala Leu Leu Val Gln Asp Gly Phe Leu Asp Leu
 65                  70                  75                  80

Asp Ala Glu Val Val Lys Tyr Trp Pro Glu Phe Gly Ala Glu Gly Lys
                 85                  90                  95

Ala Thr Ile Thr Val Ala Gln Leu Leu Ser His Gln Ala Gly Leu Leu
                100                 105                 110

Gly Val Glu Gly Gly Leu Thr Leu Ala Glu Tyr Asn Asn Ser Glu Leu
            115                 120                 125

Ala Ala Ala Lys Leu Ala Gln Met Arg Pro Leu Trp Lys Pro Gly Thr
130                 135                 140

Ala Phe Gly Tyr His Ala Leu Thr Ile Gly Val Phe Met Glu Glu Leu
145                 150                 155                 160

Cys Arg Arg Ile Thr Gly Ser Thr Leu Gln Glu Ile Tyr Glu Gln Arg
                165                 170                 175

Ile Arg Ser Val Thr Gly Ala His Phe Phe Leu Gly Leu Pro Glu Ser
            180                 185                 190

Glu Glu Pro Arg Tyr Ala Thr Leu Arg Trp Ala Ala Asp Pro Ser Gln
        195                 200                 205

Pro Trp Ile Asp Pro Ala Ser His Phe Gly Leu Ser Ala Asn Ser Ala
    210                 215                 220

Val Gly Asp Ile Leu Asp Leu Pro Asn Leu Arg Glu Val Arg Ala Ala
225                 230                 235                 240

Gly Leu Ser Ser Ala Ala Gly Val Ala Ser Ala Glu Gly Met Ala Arg
                245                 250                 255

Val Tyr Ala Ala Ala Leu Thr Gly Leu Ala Ala Asn Gly Asp Arg Ala
            260                 265                 270

Ala Val Ala Pro Leu Leu Ser Glu Glu Thr Ile Gln Thr Val Thr Ala
        275                 280                 285

Glu Gln Val Phe Gly Ile Asp Arg Val Phe Gly Glu Thr Ser Cys Phe
    290                 295                 300

Gly Thr Val Phe Met Lys Ser His Ala Arg Ser Pro Tyr Gly Ser Tyr
305                 310                 315                 320

Arg Ala Phe Gly His Asp Gly Ala Ser Ala Ser Leu Gly Phe Ala Asp
                325                 330                 335

Pro Val Tyr Glu Leu Ala Phe Gly Tyr Val Pro Gln Gln Ala Glu Pro
            340                 345                 350

Gly Gly Ala Gly Cys Arg Asn Leu Glu Leu Ser Ala Ala Val Arg Lys
        355                 360                 365

Ala Val Thr Glu Leu Ala Gln
    370                 375

<210> SEQ ID NO 4
<211> LENGTH: 1125
<212> TYPE: DNA
<213> ORGANISM: Arthrobacter globiformis
<220> FEATURE:
<221> NAME/KEY: CDS
<222> LOCATION: (1)..(1125)

<400> SEQUENCE: 4 gtg gat gca cag acg att gcc cct gga ttc gaa tca gtc gcc gaa ctc         48

```
Val Asp Ala Gln Thr Ile Ala Pro Gly Phe Glu Ser Val Ala Glu Leu
1               5                   10                  15 ttt ggc cgt ttc ctg agc gaa gac cgg gaa tat tca gcc cag ctc gcg      96
Phe Gly Arg Phe Leu Ser Glu Asp Arg Glu Tyr Ser Ala Gln Leu Ala
                20                  25                  30 gcc tac cac cgc gga gtc aag gta ttg gac atc agc ggt ggg ccg cac     144
Ala Tyr His Arg Gly Val Lys Val Leu Asp Ile Ser Gly Gly Pro His
            35                  40                  45 cgc cgc ccg gat tcc gtg acc ggt gtt ttc tcc tgc tcc aag gga gta     192
Arg Arg Pro Asp Ser Val Thr Gly Val Phe Ser Cys Ser Lys Gly Val
        50                  55                  60 tcc ggg ctg gtc atc gca ctt ttg gtc cag gac ggc ttc ctc gac ctc     240
Ser Gly Leu Val Ile Ala Leu Leu Val Gln Asp Gly Phe Leu Asp Leu
65                  70                  75                  80 gac gcc gaa gtg gtc aag tac tgg ccg gaa ttc ggc gcc gaa gga aag     288
Asp Ala Glu Val Val Lys Tyr Trp Pro Glu Phe Gly Ala Glu Gly Lys
                85                  90                  95 gcc acg att acc gtg gcc cag ctc ctc tcc cac cag gcc ggg ctt ctg     336
Ala Thr Ile Thr Val Ala Gln Leu Leu Ser His Gln Ala Gly Leu Leu
            100                 105                 110 gga gtc gaa ggc gga ctc acc ctc gcg gaa tac aac aac tcc gaa ctg     384
Gly Val Glu Gly Gly Leu Thr Leu Ala Glu Tyr Asn Asn Ser Glu Leu
        115                 120                 125 gcc gcc gcc aag ctc gcg cag atg cgg ccg ctg tgg aag ccc ggg acc     432
Ala Ala Ala Lys Leu Ala Gln Met Arg Pro Leu Trp Lys Pro Gly Thr
130                 135                 140 gcc ttc ggg tac cac gcc ctg acc atc ggc gtc ttc atg gag gag ctt     480
Ala Phe Gly Tyr His Ala Leu Thr Ile Gly Val Phe Met Glu Glu Leu
145                 150                 155                 160 tgc cgc cgg atc acc ggg tcc acg ctc cag gaa atc tac gaa cag cgg     528
Cys Arg Arg Ile Thr Gly Ser Thr Leu Gln Glu Ile Tyr Glu Gln Arg
                165                 170                 175 atc cgc tcg gtc acg ggc gcc cac ttc ttc ctg gga ctg cct gag tcc     576
Ile Arg Ser Val Thr Gly Ala His Phe Phe Leu Gly Leu Pro Glu Ser
            180                 185                 190 gag gaa ccc cgc tat gcc acc ctc cgt tgg gct gca gac ccc tcc cag     624
Glu Glu Pro Arg Tyr Ala Thr Leu Arg Trp Ala Ala Asp Pro Ser Gln
        195                 200                 205 ccg tgg att gat ccc gcc agc cat ttc ggc ctt tcc gca aac tcg gcc     672
Pro Trp Ile Asp Pro Ala Ser His Phe Gly Leu Ser Ala Asn Ser Ala
210                 215                 220 gtg ggg gac atc ctt gac ctg ccc aac ctc cgc gag gtc cgc gca gcc     720
Val Gly Asp Ile Leu Asp Leu Pro Asn Leu Arg Glu Val Arg Ala Ala
225                 230                 235                 240 ggc ctg agt tca gcc gcc gga gtc gcc agc gcg gaa ggc atg gcc cgc     768
Gly Leu Ser Ser Ala Ala Gly Val Ala Ser Ala Glu Gly Met Ala Arg
                245                 250                 255 gtc tac gct gcg gca ctc acc gga ctt gcc gcc aac ggc gac cga gcc     816
Val Tyr Ala Ala Ala Leu Thr Gly Leu Ala Ala Asn Gly Asp Arg Ala
            260                 265                 270 gcc gtc gcg ccc ctc ctc agc gaa gag acc atc caa acc gtc acg gcc     864
Ala Val Ala Pro Leu Leu Ser Glu Glu Thr Ile Gln Thr Val Thr Ala
        275                 280                 285 gag cag gtc ttc ggc atc gac cgg gtg ttc ggc gag acg agc tgc ttt     912
Glu Gln Val Phe Gly Ile Asp Arg Val Phe Gly Glu Thr Ser Cys Phe
290                 295                 300 ggg aca gtg ttc atg aaa tcg cat gca cgc tcg cct tat ggc agc tac     960
Gly Thr Val Phe Met Lys Ser His Ala Arg Ser Pro Tyr Gly Ser Tyr
305                 310                 315                 320
```

```
cgg gcg ttc ggg cac gac ggc gcc agc gca tct ttg ggg ttc gct gac    1008
Arg Ala Phe Gly His Asp Gly Ala Ser Ala Ser Leu Gly Phe Ala Asp
                    325             330                 335 cct gtg tat gaa ctc gcc ttc ggg tac gtg ccg caa cag gcc gag ccg    1056
Pro Val Tyr Glu Leu Ala Phe Gly Tyr Val Pro Gln Gln Ala Glu Pro
                340             345                 350 ggc gga gcg gga tgc cgc aac ctt gag ctg agc gcc gcc gtg cgg aag    1104
Gly Gly Ala Gly Cys Arg Asn Leu Glu Leu Ser Ala Ala Val Arg Lys
            355             360             365 gca gtc acc gaa ctg gct cag                                        1125
Ala Val Thr Glu Leu Ala Gln
    370             375
```